United States Patent
McLean

(10) Patent No.: US 9,295,565 B2
(45) Date of Patent: Mar. 29, 2016

(54) METHOD OF EXPANDING AN INTRADISCAL SPACE AND PROVIDING AN OSTEOCONDUCTIVE PATH DURING EXPANSION

(71) Applicant: SPINE WAVE, INC., Shelton, CT (US)

(72) Inventor: Scott McLean, Waterbury, CT (US)

(73) Assignee: Spine Wave, Inc., Shelton, CT (US)

( * ) Notice: Subject to any disclaimer, the term of this patent is extended or adjusted under 35 U.S.C. 154(b) by 222 days.

(21) Appl. No.: 14/057,210

(22) Filed: Oct. 18, 2013

(65) Prior Publication Data

US 2015/0112438 A1    Apr. 23, 2015

(51) Int. Cl.
*A61F 2/44* (2006.01)
*A61F 2/30* (2006.01)

(52) U.S. Cl.
CPC .............. *A61F 2/447* (2013.01); *A61F 2/4455* (2013.01); *A61F 2002/304* (2013.01); *A61F 2002/3092* (2013.01); *A61F 2002/30387* (2013.01); *A61F 2002/30556* (2013.01); *A61F 2002/30599* (2013.01)

(58) Field of Classification Search
CPC .......................................... A61F 2/4455–2/447
See application file for complete search history.

(56) References Cited

U.S. PATENT DOCUMENTS

| | | | |
|---|---|---|---|
| 4,863,476 A | 9/1989 | Shepperd | |
| 5,002,576 A | 3/1991 | Fuhrmann et al. | |
| 6,149,688 A | 11/2000 | Brosnahan et al. | |
| 6,595,998 B2 | 7/2003 | Johnson et al. | |
| 6,758,862 B2 | 7/2004 | Berry et al. | |
| 6,846,327 B2 | 1/2005 | Khandkar et al. | |
| 7,044,972 B2 | 5/2006 | Mathys, Jr. et al. | |
| 7,217,293 B2 | 5/2007 | Branch, Jr. | |
| 7,993,402 B2 | 8/2011 | Sidler | |
| 8,303,658 B2 | 11/2012 | Peterman | |
| 8,328,871 B2 | 12/2012 | Capote et al. | |
| 8,353,963 B2 | 1/2013 | Glerum | |
| 2002/0026191 A1* | 2/2002 | Dixon et al. | 606/57 |
| 2002/0143403 A1 | 10/2002 | Vaidyanathan et al. | |
| 2003/0125739 A1 | 7/2003 | Bagga et al. | |
| 2004/0243241 A1 | 12/2004 | Istephanous et al. | |
| 2005/0177238 A1 | 8/2005 | Khandkar et al. | |
| 2006/0129244 A1* | 6/2006 | Ensign | 623/17.16 |
| 2006/0271201 A1 | 11/2006 | Kumar et al. | |
| 2007/0173820 A1 | 7/2007 | Trieu | |
| 2007/0255412 A1 | 11/2007 | Hajaj et al. | |
| 2007/0270950 A1 | 11/2007 | Trieu | |

(Continued)

FOREIGN PATENT DOCUMENTS

WO    2007051307 A2    5/2007

*Primary Examiner* — David Bates
*Assistant Examiner* — Olivia C Chang
(74) *Attorney, Agent, or Firm* — Hoffmann & Baron, LLP

(57) ABSTRACT

A method is provided for expanding an intradiscal space between opposing vertebral bodies by expanding an expandable interbody fusion device and establishing an osteoconductive path between the opposing vertebral bodies through the device during expansion. The device is expanded by introducing at least one intermediate element between an upper element and a lower element to achieve ligamentotaxis. Each of the upper element, intermediate element and lower element comprises a region of porous biocompatible material coated or impregnated with material having relatively high osteoconductive and osteoinductive properties. During and upon expansion the regions are stress loaded by the opposing vertebral bodies to promote fusion between the vertebral bodies through the device.

23 Claims, 6 Drawing Sheets

(56) References Cited

U.S. PATENT DOCUMENTS

| | | |
|---|---|---|
| 2007/0293948 A1 | 12/2007 | Bagga et al. |
| 2008/0119853 A1 | 5/2008 | Felt et al. |
| 2008/0161927 A1 | 7/2008 | Savage et al. |
| 2008/0206297 A1 | 8/2008 | Roeder et al. |
| 2008/0300598 A1* | 12/2008 | Barreiro et al. ............ 606/63 |
| 2008/0319247 A1 | 12/2008 | Forbes et al. |
| 2009/0311303 A1 | 12/2009 | Lutton et al. |
| 2010/0168798 A1 | 7/2010 | Clineff et al. |
| 2010/0255053 A1 | 10/2010 | Savage-Erickson |
| 2011/0151259 A1 | 6/2011 | Jarman-Smith et al. |
| 2012/0215313 A1 | 8/2012 | Saidha et al. |
| 2012/0323339 A1 | 12/2012 | Olalde Graells et al. |
| 2013/0060230 A1 | 3/2013 | Capistron et al. |
| 2013/0066320 A1 | 3/2013 | Jarman-Smith et al. |
| 2013/0085535 A1 | 4/2013 | Greenhalgh et al. |
| 2013/0090735 A1 | 4/2013 | Mermuys et al. |
| 2013/0178900 A1 | 7/2013 | Fallin et al. |

* cited by examiner

METHOD OF EXPANDING AN INTRADISCAL SPACE AND PROVIDING AN OSTEOCONDUCTIVE PATH DURING EXPANSION

FIELD OF THE INVENTION

The subject invention relates generally to the field of spinal surgery and more particularly to a method of expanding an intradiscal space between opposing vertebral bodies with an expandable interbody fusion device and providing an osteoconductive path during expansion.

BACKGROUND OF THE INVENTION

Spinal implants such as interbody fusion devices are used to treat degenerative disc disease and other damages or defects in the spinal disc between adjacent vertebrae. The disc may be herniated or suffering from a variety of degenerative conditions, such that the anatomical function of the spinal disc is disrupted. Most prevalent surgical treatment for these conditions is to fuse the two vertebrae surrounding the affected disc. In most cases, the entire disc will be removed, except for a portion of the annulus, by way of a discectomy procedure. A spinal fusion device is then introduced into the intradiscal space and suitable bone graft or bone substitute material is placed substantially in and/or adjacent the device in order to promote fusion between two adjacent vertebrae.

Certain of these spinal interbody fusion devices are of a fixed size and configuration with a hollow internal graft chamber and openings through superior and inferior surfaces for communicating with endplates of opposing vertebral bodies. Graft material to promote fusion is typically packed into the chamber so as to facilitate fusion with the adjoining vertebral endplates through the openings. Examples of such devices are described in U.S. Pat. No. 4,834,757, issued to Brantigan on May 30, 1989 and U.S. Pat. No. 5,702,449, issued to McKay on Dec. 30, 1997. The McKay '449 patent shows a fusion implant with an outer sleeve and an interior body of porous biocompatible material for permitting bony ingrowth therethrough.

Richelsoph in U.S. Pat. No. 5,749,916, issued on May 12, 1998 noted that unless the graft material inside the device is properly stressed, the quality of the fusion may be affected. Richelsoph recognized that according to Wolf's Law bone grows along lines of stress. In Richelsoph's view the prior fixed dimension devices simply hold the vertebral bodies apart and act as spacers with the material within the devices never being stressed. In order to produce stress on the graft material Richelsoph provided a device that is flexible and has transfer means for transferring stress from the adjoining vertebrae to the graft material within the device.

It has also been recognized that fusion can be enhanced between adjacent vertebrae and graft material by stretching the ligaments attached to adjoining vertebral bodies in a process called ligamentotaxis as described, for example in U.S. Pat. No. 6,709,438, issued to Dixon et al. on Mar. 23, 2004. With ligamentotaxis the implant may be maintained in position under compression applied by adjacent vertebrae due to the tension induced in the stretched ligaments. Such compression encourages fusion by the loading of the graft interface with adjacent vertebral body endplates. In such a procedure, the graft has been of fixed dimension and placed after the opposing vertebrae had been spread.

With certain known expandable interbody fusion devices, graft material is placed within the device or the intradiscal space prior to expansion. The graft material tends to lose any stress loading within the implant as the implant is expanded. As a result, graft material is introduced into the device during or subsequent to expansion and around the expanded device. Examples of such devices include those described in U.S. Pat. No. 8,062,375, issued on to Glenn et al. on Nov. 22, 2011, U.S. Pat. No. 8,105,382, issued to Olmos et al. on Jan. 31, 2012, U.S. Pat. No. 8,382,842, issued to Greenhalgh et al. on Feb. 26, 2013, and U.S. Pat. No. 8,403,990, issued to Dryer et al. on Mar. 26, 2013. In certain other instances bone graft is introduced under pressure in an effort to stress load the graft material against the endplates of opposing vertebral bodies, as described, for example in commonly assigned PCT Application WO 2013/036707 A1, published on Mar. 14, 2013.

Accordingly, it is desirable to provide an improved expandable spinal interbody fusion device that prior to insertion contains material for promoting bone fusion and that is capable of providing and maintaining stress loading on such material during and after expansion, without the placement of additional graft material into the device during or after expansion.

SUMMARY OF THE INVENTION

It is an object of the invention to provide an improved method for expanding an intradiscal space between opposing vertebral bodies by expanding an expandable interbody fusion device and providing an osteoconductive path between the opposing vertebral bodies through the device during expansion.

DESCRIPTION OF THE EMBODIMENTS

Figure 1:
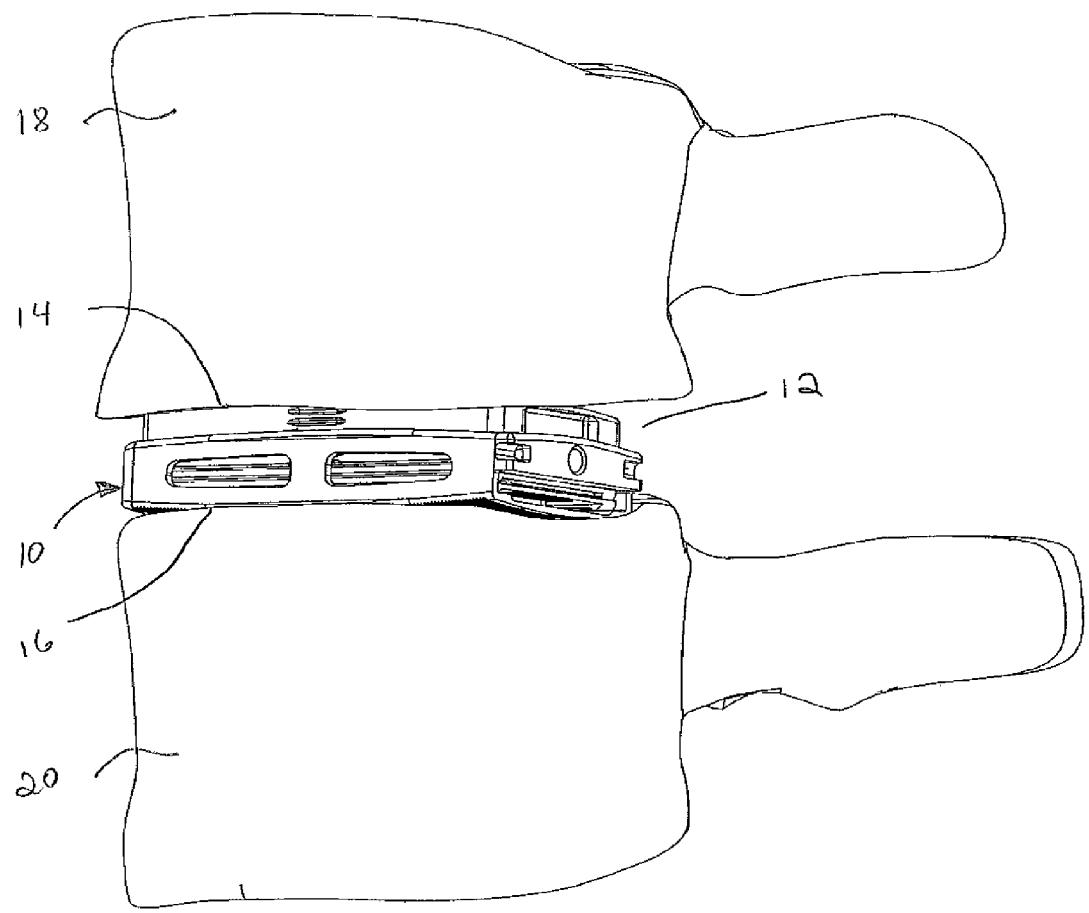
FIG. 1 is a side perspective view of a portion of a spine showing opposing vertebral bodies and the expandable interbody fusion device inserted into an intradiscal space according to one embodiment of the invention.
Figure 2:
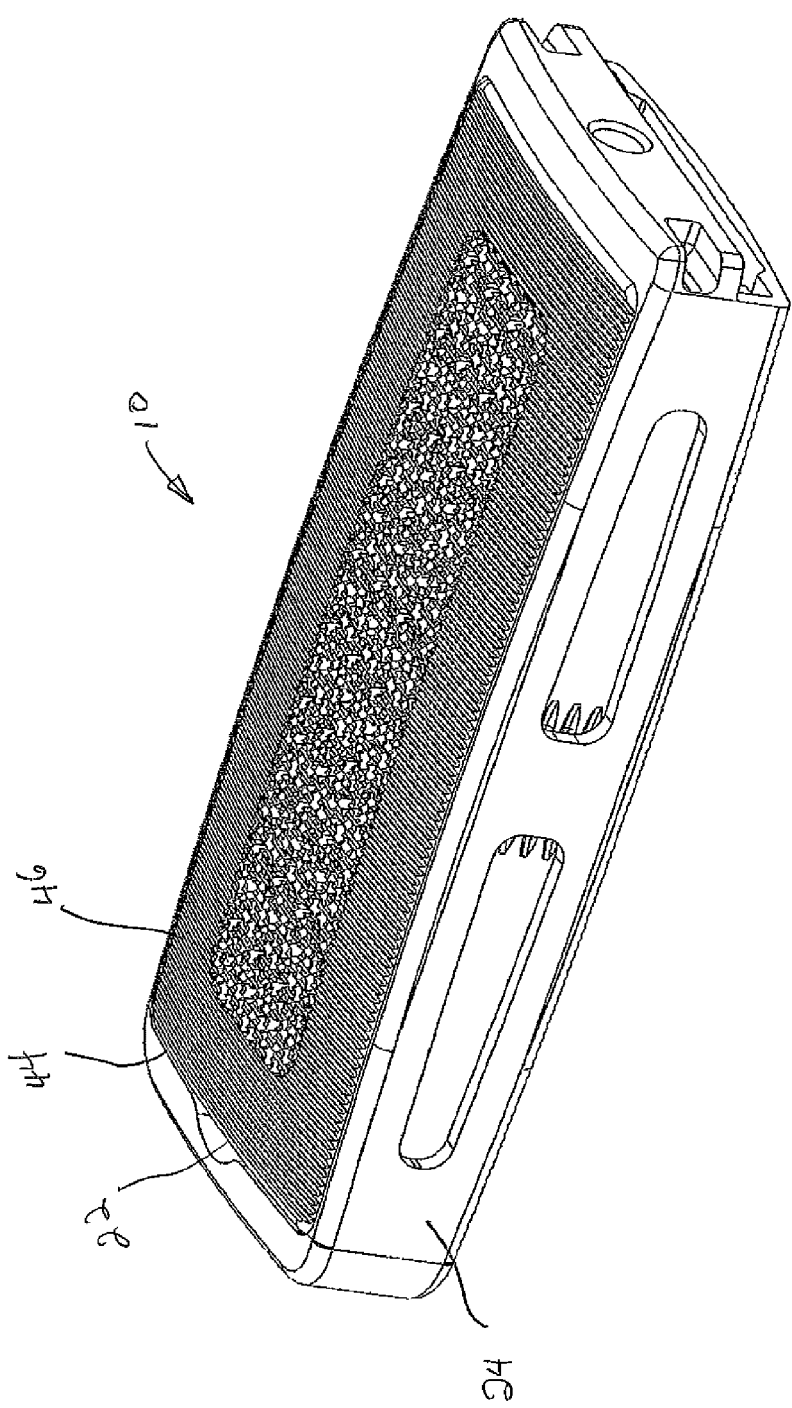
FIG. 2 is a rear perspective view of the expandable interbody fusion device of FIG. 1 in non-expanded condition.
Figure 3:
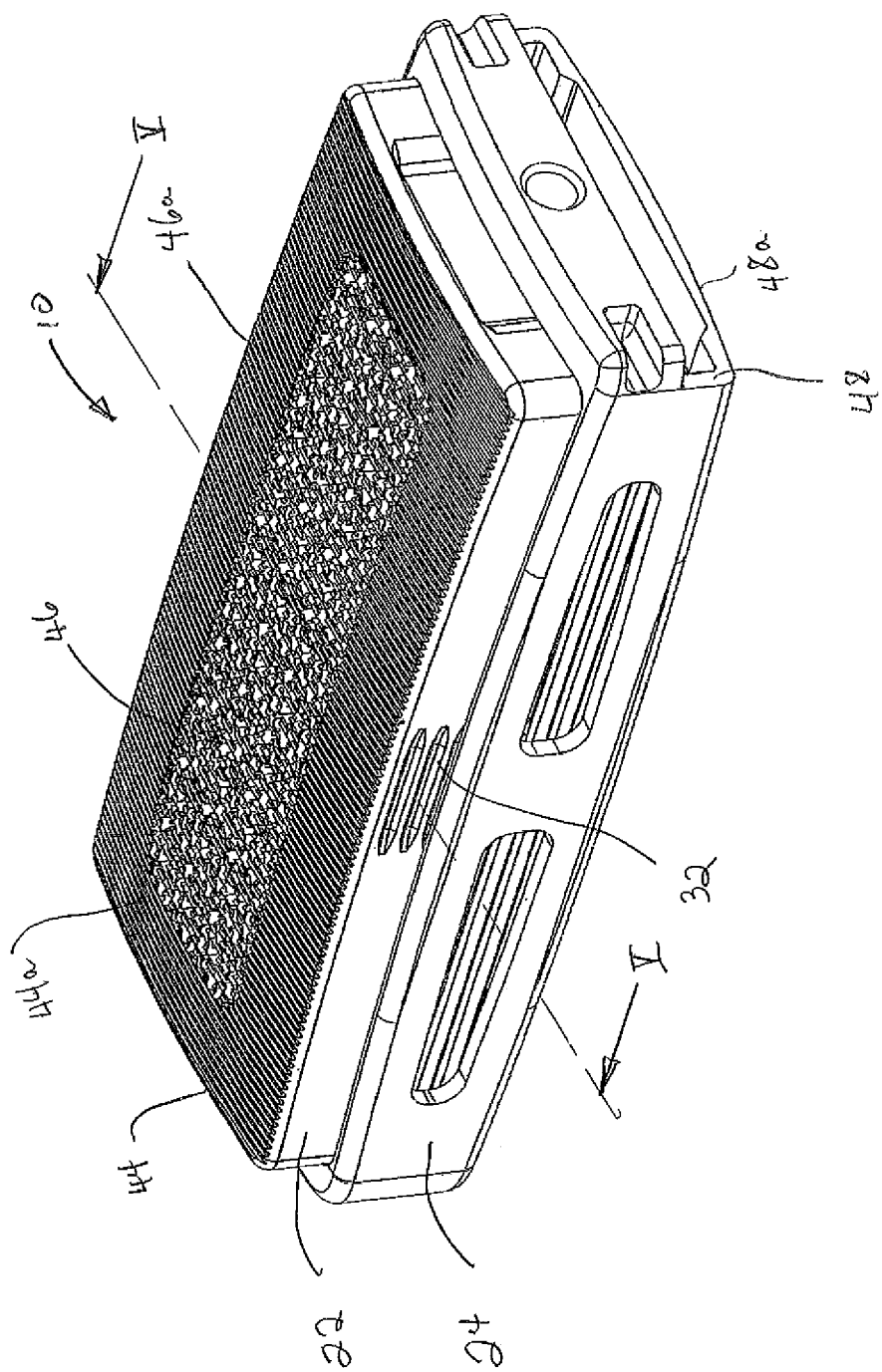
FIG. 3 is a rear perspective view of the expandable interbody fusion device of FIG. 2 in expanded condition.

For the purposes of promoting and understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

In accordance with one embodiment of the invention, an expandable interbody fusion device 10 as shown in FIG. 1 is placed in the intradiscal space 12 of a spine defined by the endplates 14 and 16 of opposing vertebral bodies 18 and 20. In this particular arrangement, device 10 is sized and configured as a lateral implant to be introduced into the intradiscal space 12 from the lateral direction. It should be understood that device 10 may also be sized and configured to be introduced posteriorly, posteriolaterally and anteriorly in accordance with the principles of the invention.

Turning now to FIGS. 2-5, details of the interbody fusion device 10 are described. Device 10 in this arrangement includes an elongate superior upper element 22, an elongate inferior lower element 24 and at least one elongate intermediate element 26, although a plurality of intermediate elements 26 may be employed, as will be described. Upper element 22 is supported by inferior element 24 for telescopic expansion during introduction of one or more intermediate elements 26. Lower element 24 includes a channel 28 for introduction of elements 26 into a fully bounded cavity 30 of lower element 24. Upper element 22 includes a series of grooves 32 for engagement with a complementary pair of opposing ribs 34 (FIG. 5) projecting interiorly of element 24 into cavity 30 for releasably holding upper element 22 and lower element 24 together during expansion. Introduction of an intermediate element 26 is sufficient to overcome the releasable retention to allow telescopic expansion of upper element 22 relative to lower element 24 as the intermediate element 26 is introduced.

Figure 4:
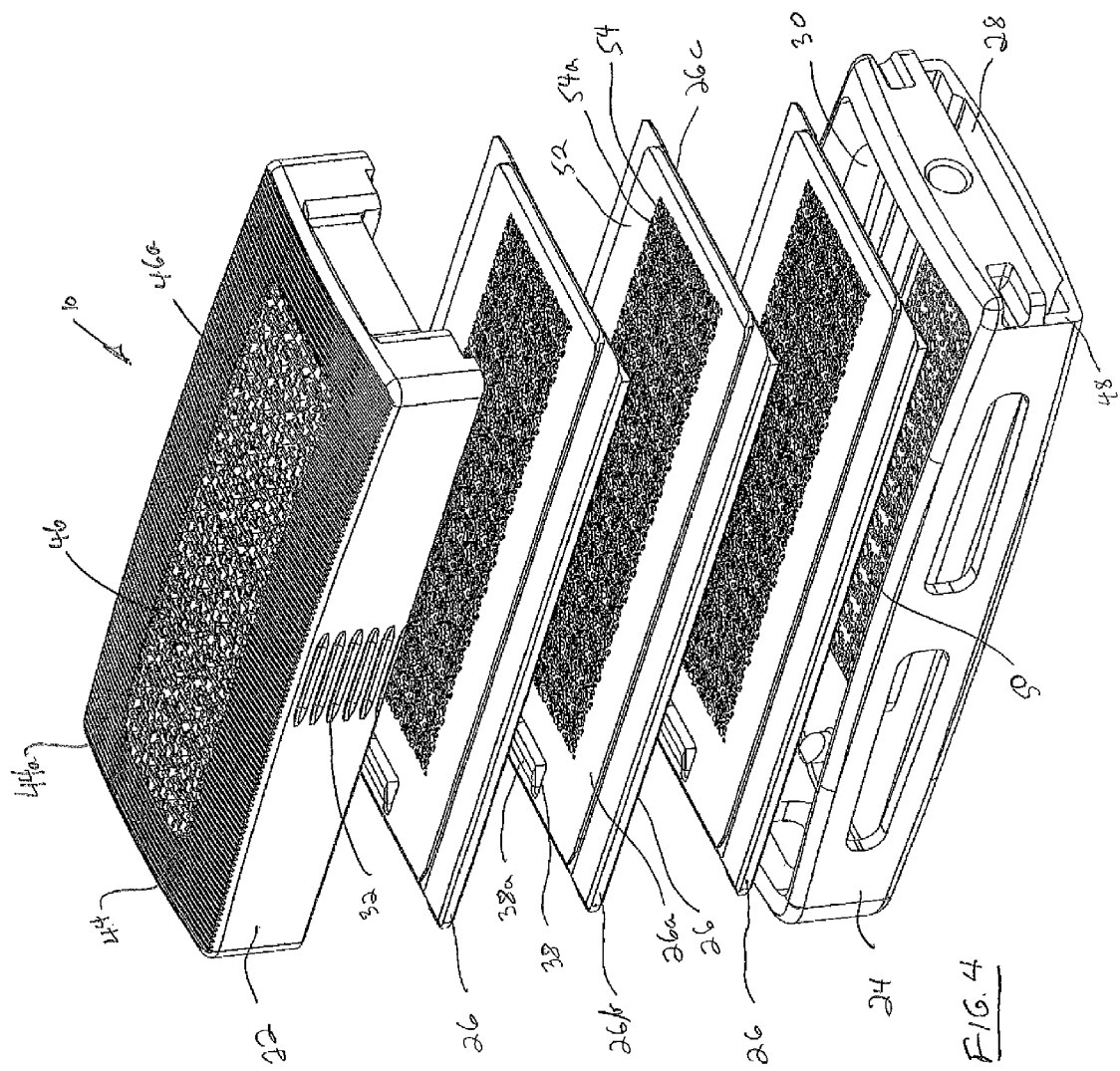
FIG. 4 is an exploded perspective view of the expandable interbody device of FIG. 3.
Figure 5:
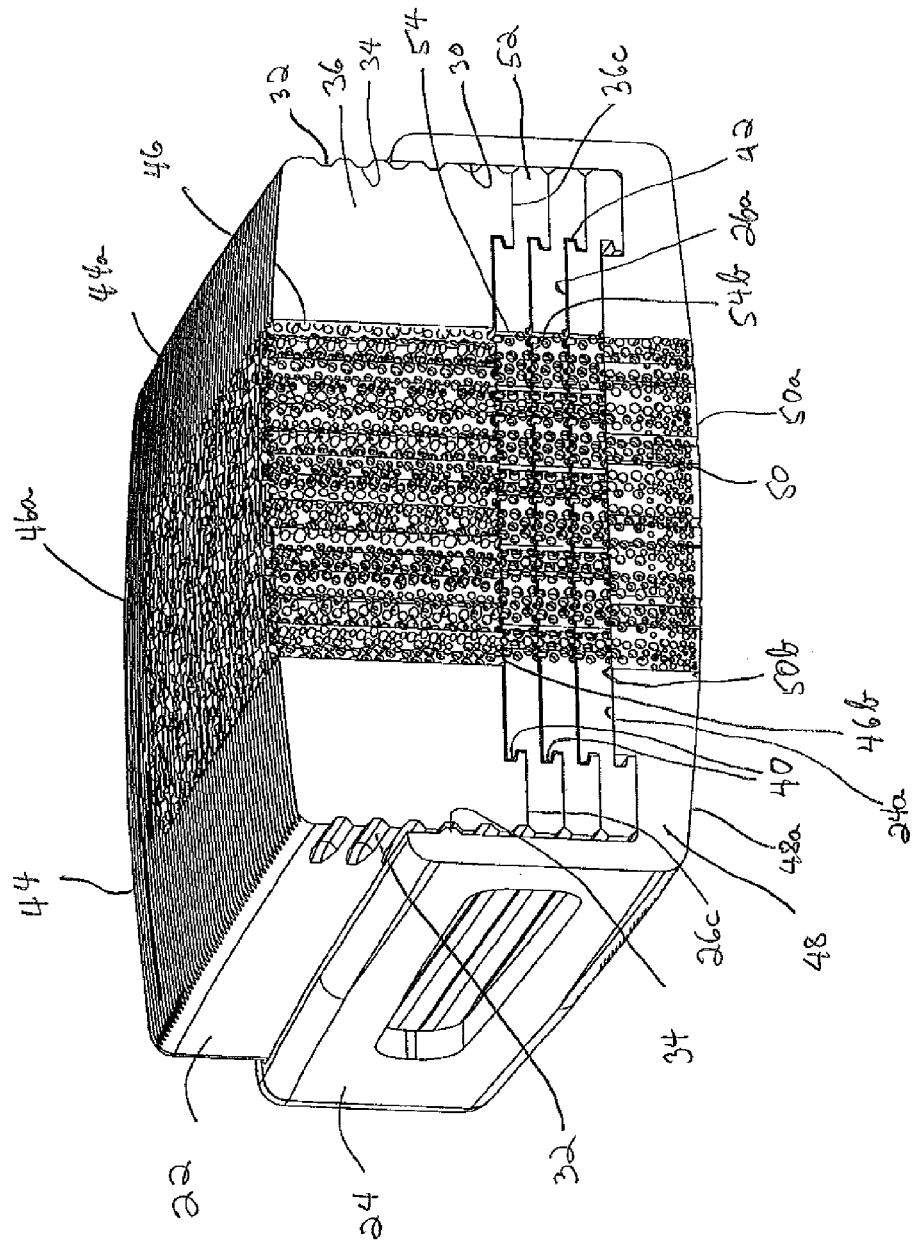
FIG. 5 is a cross section of the expandable interbody fusion device as seen along the viewing lines V-V of FIG. 3.

Intermediate element 26 as shown in FIGS. 4-5 is generally flat and, in this arrangement, in the form of a generally planar wafer. Intermediate element 26 includes several features for interlocking engagement to a hub 36 of upper element 22 and to adjacent intermediate elements 26 in a complementary interlocking mating interface. One particular feature includes at least one locking element 38 defined by a resiliently deflectable prong 38a that projects outwardly above the upper surface 26a of intermediate element 26. In one arrangement, the prong 38 is disposed at the distal end 26b of intermediate element 26 for resilient engagement with a recess (not shown) formed into distal end of the lower surface 26c of intermediate element 26 upon completion of insertion into device 10. The lower surface 36c of hub 36 and the lower surface 26c of each intermediate element 26 as shown in FIG. 5 also define a T-slot configuration 40 for mating with a T-bar configuration 42 on the upper surface 26a of an intermediate element 26. It should be appreciated that the respective T-bar and T-slot configurations may be formed on either the upper surface or the lower surface of an intermediate element as desired. The expandable interbody device 10 heretofore described is similar in structure and function to the expandable interbody devices described in commonly assigned patent applications, namely U.S. patent application Ser. No. 13/795,054, entitled "Expandable Interbody Fusion Device with Graft Chambers", filed on Mar. 12, 2013 (the '054 application), and U.S. patent application Ser. No. 13/689,046, entitled "Expandable Interbody Fusion Device with Graft Chambers", filed on Nov. 29, 2012 (the '046 application), each of which is incorporated herein by reference in its entirety.

With continued reference to FIGS. 2-5 further features of the subject invention are illustrated and described. Each of the upper element 22, lower element 24 and intermediate elements 26 is formed to have at least a region including a material for promoting bony ingrowth. Bony ingrowth means that there is biological growth of bone matter through at least the region containing the bony ingrowth material. The following description of the upper element 22 is illustrative of the formation of the regions of each of the upper element 22, lower element 24 and intermediate elements 26.

Upper element 24 comprises a body 44 surrounding a generally centrally located region 46. Body 44 and region 46 may be formed of the same or different materials. Body 44 is formed to have a structure having little or no porosity that in a preferred form, substantially mimics cortical bone. Region 46 is formed to have a structure having pores throughout for the encouragement of bony through growth. Body 44 is preferably structurally stronger than the structure of region 46 so as to provide a hard and strong load-bearing structure capable of withstanding loads on device 10 experienced in the intradiscal space. Region 46 extends fully through body 44 (FIG. 5) and includes a top surface 46a that is exposed at the upper surface 44a of upper element 22 for contact with endplate 14 for substantially optimized bony ingrowth and fusion with adjacent vertebral body 18. Region 46 includes a bottom surface 46b that is exposed adjacent the lower surface 36c of hub 26 for compressive contact with the adjacent region of the uppermost intermediate element 26, as will be described. The porous region 46 is also more radiolucent than the solid non-porous body 44 and hence provides enhanced visualization for analysis of bone growth and subsequent fusion with adjacent structures. It should be appreciated that region 46 may be other than generally centrally located on upper element 24 and that there may be more than one region 46.

In one arrangement, body 44 is made of substantially solid non-porous polyaryletherketone (PAEK) and region 46 is made of substantially porous polyaryletherketone (PAEK). More particularly, the PAEK material for both body 44 and region 46 is polyetheretherketone (PEEK). In one particular method of construction, body 44 and region 46 may be formed in a single process wherein a porous region and a non-porous region of PEEK are formed together as a unitary article. Such a process which utilizes additive layering techniques in a selective laser sintering process is described, for example, in U.S. Patent Publication 2013/0217838, published by DeFelice et al. on Aug. 22, 2013, U.S. Pat. No. 8,350,186, issued to Jones et al. on Jan. 8, 2013, and U.S. Pat. No. 7,537,664, issued to O'Neill et al. on May 26, 2009, each of which is incorporated herein by reference in its entirety. An article using such techniques may be formed as a generally flat plate having a generally centrally located region of porous PEEK and an outer surrounding border of non-porous PEEK. The plate may then be machined, for example, to the desired configuration of the finished upper element 22 having an outer body 44 and a generally central region 46, as shown in the drawing figures herein. The porous PEEK region 46 thus provides a scaffold including pores throughout that encourage bony through growth throughout region 46 and fusion to adjacent vertebral body 18.

In another particular construction, region 46 is defined by an insert that may be separately formed and attached to a separate body 44 by ultrasonic welding or by other suitable thermal processes. A porous PEEK insert 46 may be formed with a mixture of PEEK and salt (e.g. sodium chloride) in a mold cavity, compressed and heated to melt the PEEK but not the salt to form a molded part. After appropriate cooling to solidify the mixture, the molded material is placed in a water bath at an appropriate temperature to dissolve the salt from the molded part to thereby define the porous molded structure. Such a process is more fully described in PCT application WO2007/051307, internationally filed by PPD Meditech on Nov. 6, 2006 and incorporated herein by reference in its entirety.

The porous PEEK region 46 may be internally and externally coated with a bioactive coating material selected for relatively high osteoconductive and osteoinductive properties, such as resorbable hydroxyapatite or a calcium phosphate material so as to promote bony ingrowth and fusion attachment. Alternatively, the bioactive material may be impregnated within the pores of porous PEEK region 46. Such coating or impregnation may be provided after the upper element 22 is formed in a unitary process or after an insert defining region 46 is joined with body 44. Such bioactive materials would promote bony growth through the pores of region 46 and may include allograft bone, autograph bone, hydroxyapatite, bone morphologic protein, bone morphogenic protein, morselized bone or any other osteobiologic material that promotes bony through growth by, for example, osteogenesis, osteoconduction and/or osteoinduction, or any combinations thereof.

Lower element 24 comprises a body 48 surrounding a generally centrally located region 50, body 48 and region 50 being respectively formed of the same materials and in the same manner as body 44 and region 46 of element 22 described hereinabove. Region 50 extends fully through body 48 (FIG. 5) and includes a bottom surface 50a that is exposed at the lower surface 48a of lower element 24 for contact with endplate 16 for substantially optimized bony ingrowth and fusion with adjacent vertebral body 20. Region 50 includes a top surface 50b that is exposed adjacent an upwardly projecting inner surface 24a of lower element 24 for compressive contact with the adjacent region of the lowermost intermediate element 26, as will be described.

Intermediate elements 26 as described hereinabove are generally flat and are of size and configuration different from the size and configuration of upper element 22 and lower element 24. Each intermediate element 26 comprises a body 52 surrounding a generally centrally located region 54, body 52 and region 54 being respectively formed of the same materials and in the same manner as body 44 and region 46 of element 22 described hereinabove. Region 54 extends fully through body 52 (FIG. 5) and includes a top surface 54a that is exposed at the upper surface 26a of intermediate element 26 and a bottom surface 54b that is exposed at the lower surface 26c of intermediate element 26 for contact with adjacent regions, as will be described.

While PAEK and, more particularly, PEEK has been described herein as one example of a biocompatible material for the solid non-porous bodies 44, 48 and 52 and porous regions 46, 50 and 54 of upper element 22, lower element 24 and intermediate elements 26, respectively, it should be appreciated that this material is illustrative and not intended to be limiting. As such, bodies 44, 48 and 52 and regions 46, 50 and 54 may be also formed by the additive manufacturing process with other polymers known in the art, including but not limited to, polyetherketoneketone (PEKK), carbon-reinforced PEEK, polyamides, polyetherimide and polysulfone, as well as non-polymer biocompatible materials such as titanium, cobalt chrome, stainless steel and ceramics. These materials may also be used when the porous regions 46, 50 and 54 are formed as separate inserts.

Where regions 46, 50 and 54 are formed of separate inserts, bodies 44, 48 and 52 of upper element 22, lower element 24 and intermediate elements 26, respectively may be formed of other biocompatible materials including metals, polymers, ceramics or composite materials each of which would have low or no porosity. The polymers may also include those specific materials listed above with respect to the regions. Specific materials other than polymers may include solid ceramics such as aluminum oxide or alumina, zirconium oxide or zirconia and/or pyrolytic carbon.

Having described the structure and materials of device 10, the method of its use is now set forth. Device 10 includes upper element 22 and lower element 24 and one or more intermediate elements 26. Upper element 22 and lower element 24 are initially joined together as an expandable assembly on an appropriate inserter (not shown), such as the inserterer described and shown in either the '054 application or the '046 application. Upper element 22 and lower element 24 are simultaneously introduced into the intradiscal space 12 between endplates 14, 16 of respective vertebral bodies 18, 20. In the intradiscal space the upper element 22 and region 46 face and communicate with endplate 14 of vertebral body 18 and the lower element 24 and region 50 face and communicate with the endplate 16 of the opposing vertebral body 20. In the unexpanded stage, region 46 of upper element 22 and region 50 of element 24 are in substantial alignment and communication with each other.

Figure 6:
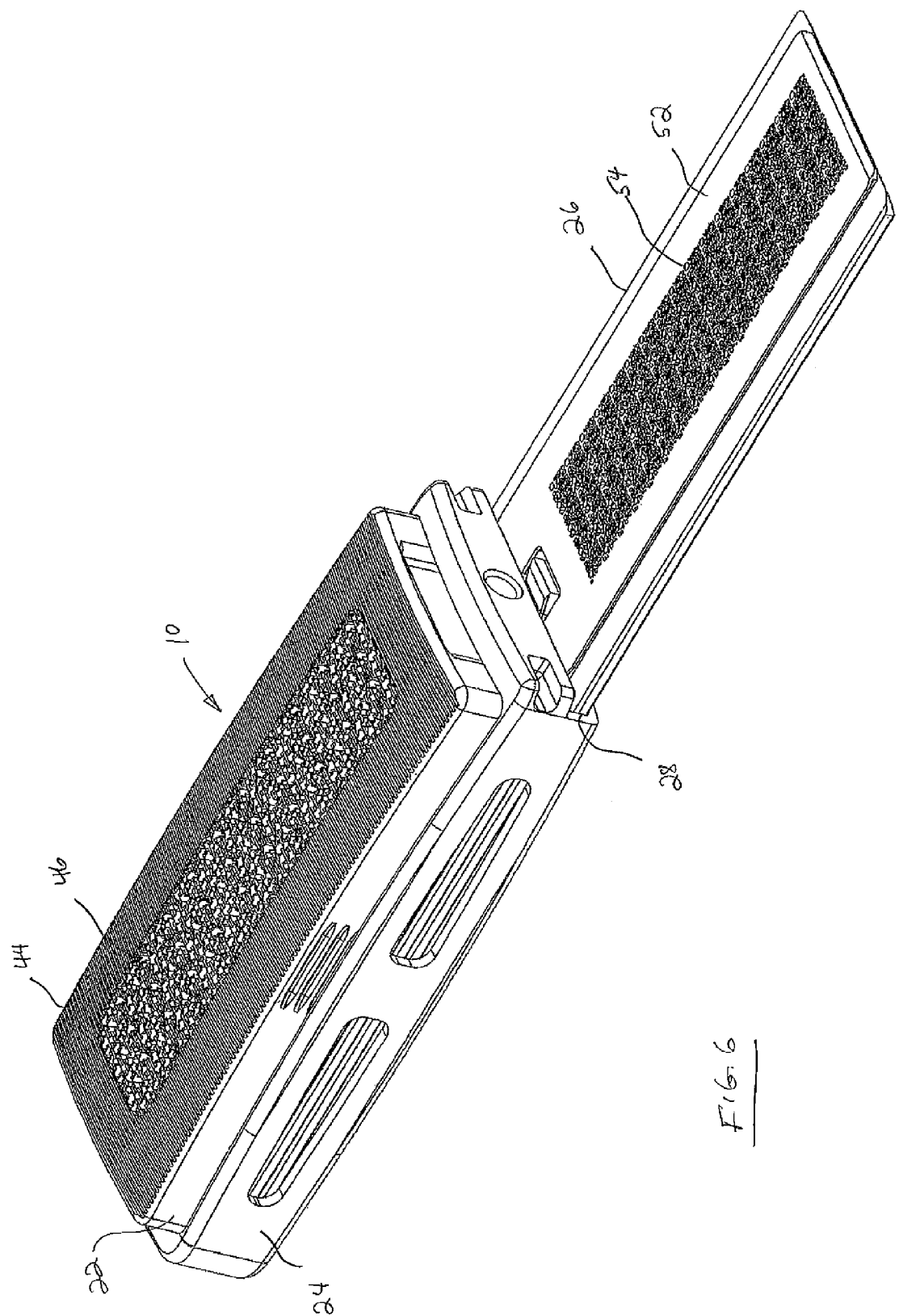
FIG. 6 is a rear perspective view of the expandable interbody fusion device of FIG. 2 showing the introduction of an element during expansion.

The device 10 is then expanded to expand the intradiscal space 12 to restore the intradiscal space 12 to, or nearly to its natural anatomical height. Expansion of device 10 is effected by introducing between upper element 22 and lower element 24 at least one intermediate element 26 in a manner as described in the '054 application or '046 application. Intermediate element 26 is introduced into the device 10 through channel 28 of lower element 24, as illustrated in FIG. 6. Alternatively, device 10 may be introduced into the intradiscal space 12 and expanded therein with an inserter such as that described in commonly assigned U.S. patent application Ser. No. 13/799,792, entitled "Inserter for Expanding an Expandable Interbody Fusion Device", filed on Mar. 13, 2013, and incorporated herein by reference in its entirety.

Introduction of an intermediate element 26 incrementally expands the height of device 10 and, depending upon the collapsed height of the intradiscal space 12, upper element 22 will be pressed against endplate 14 and lower element 24 will be pressed against endplate 16 to cause ligamentotaxis. Ligamentotaxis is achieved when the ligaments attached to adjoining vertebral bodies are stretched thereby inducing tension in the stretched ligaments. With ligamentotaxis the device 10 would be placed under compression applied by adjacent vertebrae due to the tension induced in the stretched ligaments. Such compression encourages fusion by the stress loading of the graft interface in the regions 46 and 50 with adjacent vertebral body endplates 14, 16. During introduction, region 54 of intermediate element 26 will be compressively contacted by region 46 of upper element 22 and by region 50 of lower element 24 as a result of the tension in the stretched ligaments. Upon completion of the introduction of intermediate element 26 and if ligamentotaxis is achieved, regions 46, 54 and 50 of upper element 22, intermediate element 26 and lower element 24, respectively, will all be in alignment and compressive contact. Further, region 46 of upper element 22 will be in compressive contact with endplate 14 of vertebral body 18 and region 50 of lower element 24 will be in compressive contact with endplate 16 of opposing vertebral body 20.

In the event the introduction of one intermediate element 26 is insufficient to expand the height of device 10 so as to achieve ligamentotaxis, it should be appreciated that ligamentotaxis may be achieved by the introduction of more additional elements 26. Such additional intermediate elements 26 may be sequentially introduced into the device 10 between upper element 22 and lower element 24 until ligamentotaxis and correction of the height of the intradiscal space 12 are achieved, as illustrated in FIG. 5. Subsequently introduced intermediate elements 26 may be inserted between a previously inserted intermediate element 26 and the lower element 24. During introduction, each of the regions 54 of newly inserted intermediate elements 26 will undergo compressive contact with regions 54 of an immediately adjacent previously inserted intermediate element 26 and region 50 of lower element 24.

Having expanded and corrected the intradiscal space 12 to the desired anatomical height by the incremental expansion of device 10, a stress loaded osteoconductive path between endplates 14, 16 through device 10 has been established during and upon completion of expansion of the device 10. With all the regions 46, 50 and 54 being in compressive contact with each other and with regions 46 and 50 being in compressive contact with endplates 14 and 16, respectively, there is a continuous stress loaded path of bony through growth materials to facilitate fusion with opposing vertebral bodies 18 and 20 through the pores of the porous regions 46, 50 and 54 of device 10. As such, no additional introduction of graft material into the device 10 during or after expansion of the device 10 is necessary. It should be appreciated, however, that the surgeon may choose to place additional bone graft material in the intradiscal space 12 adjacent the expanded device 10.

While the invention has been illustrated and described in detail in the drawings and foregoing description, the same should be considered as illustrative and not restrictive in character. For instance, the expandable interbody fusion device may be formed by a plurality of elements each of which is formed as the intermediate element 26 described herinabove. Accordingly, such elements would all of be of substantially the same size and configuration, each of which would be introduced sequentially between endplates 14, 16 of opposing vertebral bodies 18, 20 in a manner as described in commonly assigned U.S. Pat. No. 6,595,998 entitled "Tissue Distraction Device", which issued on Jul. 22, 2003, and which is incorporated herein by reference in its entirety. Subsequently introduced elements of this type may be inserted either below or atop a previously introduced element to provide incremental expansion. Sufficient elements may be placed until ligamentotaxis is achieved such that a region 54 of each element subsequently introduced is in compressive contact with a region 54 of a previously introduced element during and after introduction. The region 54 of the uppermost element would be in compressive contact with endplate 14 and the region 54 of the lowermost element would be in compressive contact with endplate 16. It is therefore understood that only the preferred embodiments have been presented and that all changes, modifications and further applications that come within the spirit of the invention are desired to be protected.

What is claimed is:

1. In a method of expanding an intradiscal space between opposing vertebral bodies of a spine by expanding an interbody fusion device between the endplates of the opposing vertebral bodies, the improvement comprising the step of:
incrementally expanding said device by the sequential introduction of a plurality of elements, each of said elements comprising a body defined by an outer border surrounding a generally central region consisting essentially of porous biocompatible material having pores throughout for bony through growth, said outer border and said region forming said element prior to introduction into said device, said outer border being structurally stronger than said region and consisting essentially of a solid, relatively non-porous biocompatible material; and
providing a stress loaded osteoconductive path through said interbody fusion device during expansion of said device by arranging said regions upon introduction to be in contact with each other between said endplates of said opposing vertebral bodies, the region of one element being in compressive contact with the endplate of one vertebral body and the region of another element being in compressive contact with the endplate of the opposing vertebral body.

2. The improvement of device of claim 1, wherein the provision of said stress loaded osteoconductive path includes the achievement of ligamentotaxis.

3. The improvement of device of claim 2, wherein the achievement of ligamentotaxis is provided by the incremental expansion of said expandable interbody device.

4. The method of claim 1, wherein each said region is defined by an insert separate from said body, said body and said insert being joined together to form said element.

5. The method of claim 1, wherein said solid, relatively non-porous material of said border comprises PAEK having little or no porosity.

6. The method of claim 5, wherein said porous biocompatible material of said region comprises porous PAEK.

7. The method of claim 6, wherein said bony through growth material comprises a bioactive material having relatively high osteoconductive and osteoinductive properties.

8. The method of claim 7, wherein said bioactive material is coated internally and externally on said region.

9. The method of claim 7, wherein said bioactive material is impregnated within the pores of said region.

10. The method of claim 7, wherein each said element is elongate and has an upper surface and a lower surface, said region extending through said body and having a top surface exposed at said upper surface of said element and a bottom surface exposed at said lower surface of said element.

11. The method of claim 10, wherein a pair of elements respectively defining an upper element and a lower element are introduced simultaneously and said plurality of elements define intermediate elements that are subsequently sequentially introduced between said upper element and said lower element, said regions of said upper element, said lower element and said intermediate elements being substantially aligned and in compressive contact with each other, said region of said upper element being in compressive contact with an endplate of one vertebral body and said region of said lower element being in compressive contact with the endplate of said opposing vertebral body.

12. The method of claim 11, wherein said upper element and said intermediate element are of different sizes and configurations, said intermediate element being generally flat.

13. A method of expanding an intradiscal space between two opposing vertebral bodies of the spine and establishing a stress loaded osteoconductive path therebetween during expansion, comprising the steps of;
introducing into said intradiscal space an expandable interbody fusion device comprising an upper element and a lower element, each of said upper element and said lower element comprising a body and a region of different porosities, each region comprising a porous biocompatible material and a material for promoting bony through growth, said region of each of said upper element and said lower element extending through the respective bodies of said upper element and said lower element and being in substantial alignment with each other, said device being placed such that the region of said upper element faces and communicates with the endplate of one vertebral body and the region of said lower element faces and communicates with the endplate of the opposing vertebral body; and
introducing at least one intermediate element into said interbody fusion device between said upper element and said lower element to achieve ligamentotaxis, said at least one intermediate element including an outer border surrounding a generally central region consisting essentially of porous biocompatible material having pores throughout for bony through growth, said outer border being structurally stronger and formed of material different than said generally central region and consisting essentially of a solid, relatively non-porous biocompatible material, said generally central region being defined by an insert being attached to said body outer border, said insert and said outer border forming said at least one intermediate element prior to introduction into said device, said intermediate element being placed such that said generally central region of said intermediate element is in compressive contact with the regions of both said upper element and said lower element, said region of said upper element is in compressive contact with the endplate of one vertebral body and the region of said lower element is in compressive contact with the endplate of said opposing vertebral body.

14. The method of claim 13, wherein said body of each of said upper element and said lower element is structurally stronger than the regions of said upper element and said lower element.

15. The method of claim 14, wherein the body of each of said upper element and said lower element is formed of a material comprising solid PAEK having little or no porosity.

16. The method of claim 15, wherein the region of each of said upper element and said lower element is formed of a material comprising porous PAEK having pores throughout for bony through growth.

17. The method of claim 16, wherein each of the regions of said upper element and said lower element and the region of said at least one intermediate element comprises a bioactive material having relatively high osteoconductive and osteoinductive properties.

18. The method of claim 17, wherein more than one intermediate element is introduced into said interbody fusion device to achieve ligamentotaxis, said intermediate elements being introduced sequentially between said upper element and said lower element, a subsequently introduced element being introduced one of below and atop a previously introduced intermediate element, the region of said subsequently introduced element being in compressive contact with the region of said previously introduced element and with the region of one of said upper element and said lower element.

19. The method of claim 18, wherein the border of each of said intermediate elements is formed of a material comprising solid PAEK.

20. The method of claim 19, wherein the region of each of said intermediate elements is formed of a material comprising porous PAEK.

21. The method of claim 20, wherein each intermediate element is elongate and generally flat having an upper surface and a lower surface, each of said regions extending through said respective bodies and having a top surface exposed at said upper surface of said elements and a bottom surface exposed at the lower surface of said elements.

22. The method of claim 18, wherein each of said intermediate elements respectively comprises said insert, each of said regions of said intermediate elements being respectively defined by said respective insert.

23. The method of claim 20, wherein the PAEK material of the body of each of the upper element, lower element and each intermediate element is PEEK and the PAEK material of the region of each of the upper element, lower element and each intermediate element is PEEK.

* * * * *